April 13, 1965 H. W. MOTZKAU Plant Pat. 2,492
AZALEA PLANT
Filed Aug. 22, 1963
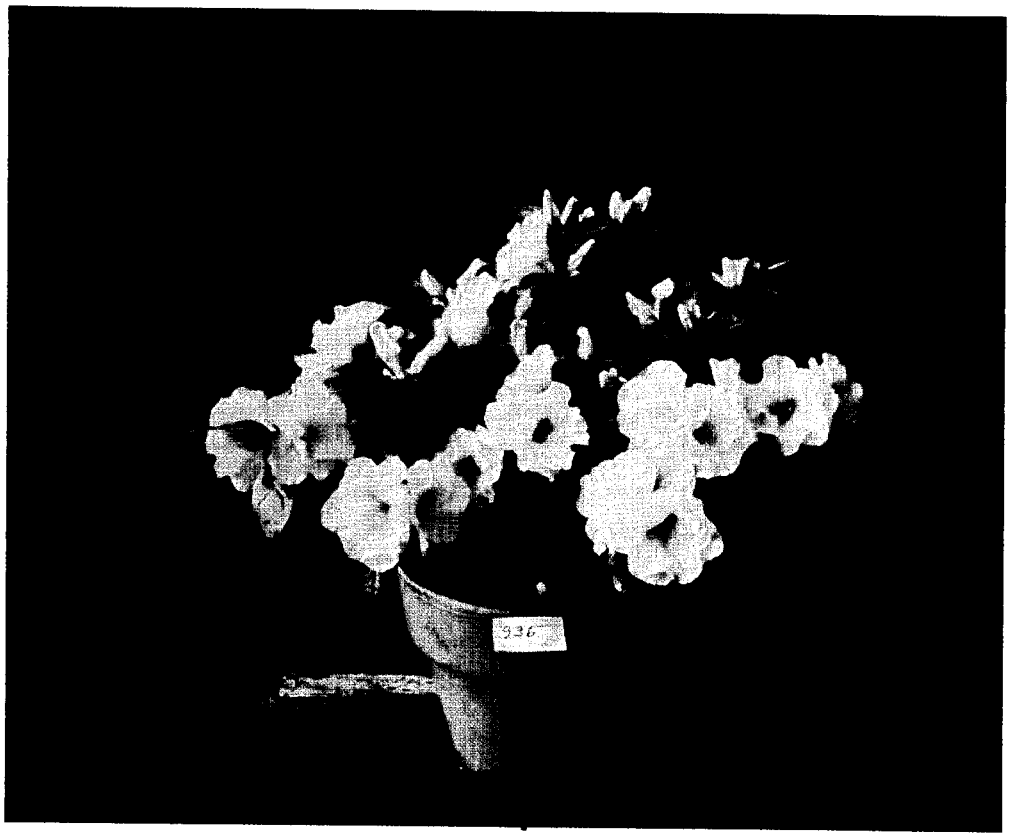
INVENTOR
H. W. MOTZKAU
BY
Robb & Robb
attorneys United States Patent Office Plant Pat. 2,492
Patented Apr. 13, 1965

2,492
AZALEA PLANT

Henry W. Motzkau, Whitewater, Wis., assignor to Yoder Brothers, Inc., Barberton, Ohio, a corporation of Ohio Filed Aug. 22, 1963, Ser. No. 303,976
1 Claim. (Cl. Plt.—57)

My present invention comprises a new and distinct variety of azalea plant which is the result of crossing a variety of my own origination known by me as #524 (an unpatented variety) with another seedling, likewise unpatented, which I identify as #631.

The object of this invention is to produce a new variety of azalea plant which is superior to either parent, deriving certain attributes such as the brighter red ultimate color from one parent with the strong growing habit from the other, certain of the other features being the result of the long program of hybridization which has been conducted by me. The plant itself is more compact and has other features which serve to distinguish it from its parents and from other varieties.

The present new variety of azalea is a selection from the results of many generations of crossing nameless seedlings which in turn were the results of crossing and inter-crossing *Azalea kurume, Azalea indica* and *Rhododendron catawbiense,* the instant variety having been selected primarily because of its color as before indicated.

As a result of the specific hybridization previously mentioned, my present new and distinct variety of azalea has been produced and is characterized by the more vivid warmer red color of its blooms, the retention of the color during the life of the bloom, the longer life of the bloom, the more uniformly compact shape of the plant, better breaking qualities, and the ability to finish the plant heavily budded although the specimens themselves are smaller.

More specifically the blooms of my new variety are of a red, between a vivid red and strong red (Nickerson Color Fan published by The Munsell Color Company), the center of the bloom having the appearance of the vivid red infused with a strong red. As grown in the vicinity of Whitewater, Wisconsin, under uniform culture, plants of this variety are grown to an average height of about 8 inches in two years with a spread of about 10 inches in a like period.

My new variety is a good keeper, with ability to bloom for a period of about one month depending on the temperature, and is susceptible of being forced for Christmas display or retarded until April.

My new variety when grown in the region of Whitewater, Wisconsin, is vigorous with medium size foliage of abundant quantity which is not affected by hot or wet weather to any great extent where normal weather conditions persist, the petals being soft and of the colors hereinbefore indicated tending to hang on and dry and darken somewhat at the end of the third week before wilting there being no fragrance and the lastingness being greater on the plant as would be expected than as a cut flower.

My new variety has been asexually reproduced by cuttings of tips or sections of branches in the vicinity of Whitewater, Wisconsin, and said new variety has been found to retain its distinctive characteristics through successve asexual reproduction.

The accompanying drawing forming a part hereof shows a typical plant of my new variety of azalea.

The following is a detailed description of my new variety of azalea plant, the color references being to the Nickerson Color Fan published by the Munsell Color Company:

*Description*

Parentage: Seedlings #524 and #631 (unpatented, my own hybridization).

Classification: Botanic—*Rhododendron hybrida.*

*Flower*

Blooming habit: Early through mid-season and profusely. Observations were made in the vicinity of Whitewater, Wisconsin during January in the greenhouse.

Bud:
- *Size.*—Medium.
- *Form.*—Urn-like.
- The bud is not affected by normal weather or hot weather.

Color:
- *When sepals first divide.*—Vivid red 5R 5/13.
- *When petals begin to unfurl.*—Slightly darker than above.
- *Sepals.*—Smooth edge—drop as bud opens.
- *Peduncle.* — Length — short. Aspect — smooth. Strength—stiff. Bud opens well.

Bloom:
- *Size.*—Medium; average size when fully expanded about 2½".
- *Borne.*—Several together.
- *Stems.*—Short, strong.
- *Form.*—When first open—cupped. Permanence—retains its form to the end.
- *Petalage.*—Semi-single—hose in hose. Number of petals under normal conditions:—five lobed—two funnels.
- *Color.*—Center of flower—5R 5/13 infused with 5R 4/12. Outer petals—Vivid red 5R 5/13. Reverse of petals—same color slightly less luminous. General tonality from a distance—between 5R 5/13 and 5R 4/12 vivid red and strong red respectively.
- *Discoloration.*—Third week—darkens before wilting.

Petals:
- *Texture.*—Soft; not affected by hot or wet weather.
- *Appearance.*—Inside—satiny. Outside—less satiny.
- *Form.*—Scalloped.
- *Arrangement.*—Hose in hose.
- *Petaloids in center.*—None.
- *Persistence.*—Hang on and dry.
- *Fragrance.*—None.
- *Lastingness.*—On the plant—long. As cut flower—fair.

Genital organs:
- *Stamens, anthers.*—Degenerated, almost none.
- *Ovaries.*—All enclosed in calyx.

Fruit:
- None; variety is sterile with its own pollen.

Plant:
- *Form.*—Bush.
- *Growth.*—Vigorous and compact.
- *Height.*—Approximately 8" in two years.
- *Spread.*—10" in two years.

Foliage:

*Size.*—Average matured leaves about 2″ long and 1¼″ wide. Petiole about ½″ long.

*Quantity.*—Abundant.

*Color.*—Upper side—Strong yellow green 7.5GY 6/8 to 5/7. Under side—Strong yellow green 10GY 6/9 to 5/8.

*Shape.*—Oval pointed.

*Texture.*—Upper side—glossy.

*Ribs and veins.*—Light, impressed.

*Edge.*—Smooth.

Wood (new):

*Color.*—Strong yellow green 7.5GY 6/9.

*Bark.*—Smooth.

I claim:

A new and distinct variety of azalea plant substantially as herein disclosed, characterized as to novelty by the more vivid warmer red color of its blooms, the retention of the color during the life of the blooms, the longer life of the blooms, the more uniformly compact shape of the plant, better breaking qualities, and the ability to finish the plant heavily budded in smaller specimens.

No references cited.

T. GRAHAM CRAVER, *Primary Examiner.*

ABRAHAM G. STONE, *Examiner.*